United States Patent [19]
Yui et al.

[11] Patent Number: 5,916,266
[45] Date of Patent: Jun. 29, 1999

[54] RAW MEMBRANOUS MATERIAL FOR MEDICAL MATERIALS AND MANUFACTURING METHODS THEREOF

[75] Inventors: Tooru Yui, Fujisawa; Tokuzo Nakagawa, Kanagawa; Kazuo Kondoh, Tokorozawa, all of Japan

[73] Assignee: Bio-Engineering Laboratories, Ltd., Tokyo, Japan

[21] Appl. No.: 08/929,399

[22] Filed: Sep. 15, 1997

Related U.S. Application Data

[63] Continuation of application No. 08/631,772, Apr. 12, 1996, abandoned.

[30] Foreign Application Priority Data

Oct. 31, 1995 [JP] Japan .................................. 7-305261

[51] Int. Cl.⁶ .................................................. A61F 2/02
[52] U.S. Cl. .............................. 623/11; 623/15; 623/66; 424/422; 424/423
[58] Field of Search ............................. 623/1, 2, 7, 8, 623/11, 12, 15, 16, 66; 435/1, 240.2, 240.3; 424/422, 423

[56] References Cited

U.S. PATENT DOCUMENTS

| | | | |
|---|---|---|---|
| 4,361,552 | 11/1982 | Baur, Jr. ................................ | 424/105 |
| 4,776,853 | 10/1988 | Klement et al. ........................... | 623/1 |
| 4,801,299 | 1/1989 | Brendel et al. ............................ | 623/1 |

FOREIGN PATENT DOCUMENTS

| | | |
|---|---|---|
| 2055099 | 5/1993 | Canada . |
| 0 306 256 | 3/1989 | European Pat. Off. . |
| 0 637 452 | 2/1995 | European Pat. Off. . |
| 0 669 138 | 8/1995 | European Pat. Off. . |
| 0 734 736 | 10/1996 | European Pat. Off. . |
| WO 93/10722 | 6/1993 | WIPO . |
| WO 95/18638 | 7/1995 | WIPO . |

Primary Examiner—David H. Willse
Assistant Examiner—Dinh X. Nguyen
Attorney, Agent, or Firm—Oblon, Spivak, McClelland, Maier & Neustadt, P.C.

[57] ABSTRACT

A raw membrane material having an acellular nature and consisting substantially of a compact layer whose characteristic matrix structure is retained intact and which is produced by dissolving and removing cellular layers including epithelium and fibroblast layers from a biogenic, connective tissue membrane which comprises epithelial, basement membrane, compact and fibroblast layer.

9 Claims, 2 Drawing Sheets

RAW MEMBRANOUS MATERIAL FOR MEDICAL MATERIALS AND MANUFACTURING METHODS THEREOF

This application is a Continuation of application Ser. No. 08/631,772, filed on Apr. 12, 1996, now abandoned.

BACKGROUND OF THE INVENTION

1. Field of the Invention

The present invention relates to a raw membrane material for medical use and to a method for producing the same.

The invention aims to supply medical raw materials that satisfy conditions which ultimate ideal artificial organs and tissues must possess. The ultimate ideal artificial organs and tissues are artificial materials for treatment, which are applied to the body during surgery and which possess not only mechanical functions, but also the physiological functions of regeneration of homologous materials and defective tissues at lesions. The artificial materials are degraded, absorbed into tissues and replaced simultaneously by normal tissues at lesions, that is, with the synchronous regeneration of defective tissue. These artificial materials are called homologous medical materials for replacement.

2. Discussion of the Prior Art

As reported In scientific papers entitled "The Extracellular Matrix of Human Amniotic Epithelium: Ultrastructure, Composition and Deposition" (J. Cell. Sci., 79: 119–136, 1985) and "Surface Visualization of Tissue Interfaces by Scanning Electron Microscopy: Methods for Exposure of Basal Lamina and Associated Structure In Human Amnion" (Scanning Microscopy Vol. 2, No. 4, Pages 2067–2078, 1988) both written by T. D. Allen and his collaborators at the Department of Ultrastructure, Paterson Institute for Cancer Research, Christie Hospital, Manchester M20 9BK, UK, T. D. Allen et al. studied in detail, using electron microscopic technique, the structure of epithelial, basal, compact and fibroblast layers of human amnion and investigated other substances that comprise the human amnion. The procedures, measures and techniques used by these authors to eliminate cells in their research are summarized below.

Fetal membranes were detached using scissors from placenta of 37–39 weeks gestation that had been removed by cesarean section. The detached fetal membranes were washed 3 times with 100–150 ml phosphate buffered saline. Amnion was separated from chorion using a forceps, after the fetal membrane was heated in phosphate buffered saline for 15–20 minutes in order to relax the adhesion between the two membranes. Washed amnion was treated with 0.2 M ammonium solution approximately 20 times every 5–15 minutes using fresh solution with each treatment. Then, the amnion was treated with 0.2% or 0.1% sodium dodecylsulphate solution for 30 minutes to 2 hours, and then treated with the protease, trypsin. Using the procedure and measures summarized above, a layer of an acellular nature comprising the basement membrane and the compact layer without cells was acquired. The two acellular layers are comprehensively called a basement membrane in microscopic science, and are separately referred to as a basement membrane layer and as a compact layer in physiology. This is the technique used by T. D. Allen et al.

Japanese Patent No. 1,842,777 (Japanese Patent Publication No. 5-50295 i.e., 50295/93), filed claiming convention priority based on U.S. patent application Ser. No. 503,203 of Jun. 10, 1983 and convention priority based on U.S. patent application Ser. No. 582,504 of Feb. 22, 1984, is entitled "Grafts Comprising Extracellular Matrix and Procedure and Method of Manufacturing and Use of Said Grafts". The patent claims: (1) Aseptic grafts comprising biogenic structural bodies, which primarily comprise collagen and elastin and which are in the form of an extracellular matrix in which cell membrane, nucleic acid, lipid and components of cytoplasm have been removed. (2) The graft as claimed in Claim 1 which has a dimension and size such as to conform to tissue structures at sites of the body to which the graft is to be implanted. (3) The aseptic graft as claimed in Claim 1, which has been treated with a detergent immediately after the above-mentioned biogenic structural bodies are removed from body and prior to substantial chemical cross-linking or subsequent changes. The patent contains 28 claims.

In the above-mentioned patent, "graft" and "biogenic structural bodies" are not limited to specific bodies but they may be derived from any living bodies. Long before the above-mentioned patent was applied for, medical products of graft derived from fish, swine or horse, which are similar to those described in the above-mentioned patent, had been on the market throughout the world. Examples are air-bladders of fish, swine pericardium and equine pericardial membranes. These are aseptic grafts comprising biogenic structural bodies which have collagen and elastin as the primary component and are in the form of an extracellular matrix without substances that form cells. In addition, they are products with dimension and sizes that conform to tissue structures at the sites of the body to which the products are applied.

A study published by Kimoto, Sugie, Tsunoda et al. of University of Tokyo in Arch. Surg. 69 (4): 549–563, 1954 and "The use of arterial implants prepared by enzymatic modification of arterial heterografts" by Rosenburg N. et al. in Arch. Surg. 74: 89, 1957, reports the procedure and methods of manufacturing and using grafts that have conditions defined with similar terms as described in claims 1 and 2 of the above-mentioned patent.

U.K. Patent No. 1,565,340 filed Apr. 25, 1978 preceded that of the above-mentioned Japanese Patent No. 1,842,777. Claim 1 of U.K. Patent No. 1,565,340 describes "Fibrous tissue materials of human or animal origin that do not substantially contain antigenic non-fibrous protein and do not substantially contain antigenic polysaccharides or glycoprotein, and that are used as a temporary bandage for skin wounds and soft tissue damages and are suited for heterografts." This invention, in light of medical and biochemical knowledge, is synonymous with "Grafts comprising biogenic structural bodies which primarily comprise collagen and elastin and which are in the form of extracellular matrix in which cell membrane, nucleic acid, lipid and components of cytoplasm have been removed" of the above-mentioned Japanese Patent No. 1,842,777. Furthermore, the detailed description of both patents shows clearly that the objects of both inventions are to provide essentially the same medical materials.

The objects of the reports and patents described above, from a scientific point of view, are to produce similar medical materials. However, different technical measures are employed individually. The technique characteristic in the abovementioned Japanese Patent No. 1,842,777 is interpreted as the procedure and method of using a detergent, which is described in Claims 3 to 26.

The prior art technique described above, which is to acquire objective medical materials, makes use of an inorganic alkaline aqueous solution, a synthetic detergent, trypsin, which is an animal protease, or ficin, which is a plant protease.

However, prior art techniques have been unable to produce a membrane material that is asymmetrical at the front and back sides and that completely satisfies "cell proliferation and cell matrix" which is characteristic of the compact layer membrane of biogenic connective tissue and is a theme in connective tissue science. In other words, prior art techniques have been unable to produce medical materials having physiological function of growing tissue cells necessary for auto-regeneration and repair of damaged tissues and of degradation, absorption and replacement in synchrony with regeneration of tissues.

Development of techniques has been sought eagerly for the manufacturing of membranous materials that have physiological functions of facilitating intake and proliferation of tissue cells, and of degradation, absorption and replacement with regenerated tissues in synchrony with regeneration of damaged tissues. The membranous materials originate from biogenic connective tissue membranes and retain the same form and structure as those of living tissue.

SUMMARY OF THE INVENTION

The present inventors endeavored to solve the abovementioned problems and completed the invention.

A first aspect of the present invention provides a raw membrane material, which is useful for the preparation of medical materials, which raw membrane material is of an acellular nature and consists essentially of a compact layer whose characteristic matrix structure is retained intact and which is produced by dissolving and removing cellular layers including epithelium and fibroblast layers from biogenic connective tissue membrane which comprises epithelium, basement membrane, compact and fibroblast layers.

A second aspect of the present invention provides a method for manufacturing the membrane material. The process comprises:

(i) positively charging and denaturing the biogenic connective tissue which comprises epithelium, basement membrane, compact and fibroblast layers with an aqueous solution of a quaternary ammonium salt of the formula:

wherein R is an alkyl group of 8 to 18 carbon atoms, (ii) then, treating the biogenic connective tissue at a near neutral pH value with thiolprotease which is a glycoprotein having a molecular weight of approximately 26,000 and an isoelectric point of 9, and (iii) thereafter, subjecting the biogenic connective tissue to ultrasonic washing.

R in the above formula is an alkyl group of 8 to 18 carbon atoms represented by the formulae $C_8H_{17}$–$C_{18}H_{37}$, and $C_{12}H_{25}$ and $C_{14}H_{29}$ are most preferred. $Cl^-$ may be replaced by other non-toxic ions.

BRIEF DESCRIPTION OF THE DRAWINGS

The invention may be better understood when the specification is read with reference to the accompanying drawings, in which.

DESCRIPTION OF PREFERRED EMBODIMENTS

Figure 1:
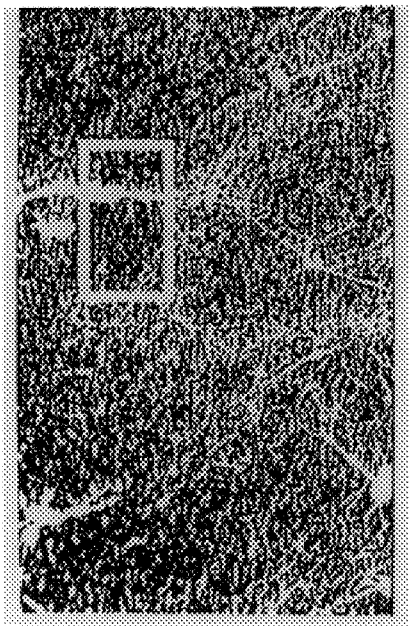
FIG. 1 is an electron microscopy photograph (1,000×), of the front surface of the product produced in Example 1.

In the field of physiology, connective tissue is classified by function and is divided into four layers, which are the epithelium, basement membrane, compact and fibroblast layers in order to study the structural form. In the field of microscopic science, connective tissue is classified visually and divided into three layers, i.e., epithelium, basement membrane and fibroblast layers. That is to say, the basement membrane layer and compact layer which are considered as different in physiology are collectively called the basement membrane in microscopic science. Also, the epithelial and fibroblast layers are of a cellular nature and the basement membrane and compact layers are of an acellular nature. The thickness of the basement membrane layer is extremely small and is expressed in nanometers, while that of the compact layer can be expressed in micrometers.

The term "connective tissue" in the present specification, includes dura mater encephali, pericardium, pleura, pelvic peritoneum, diaphragm, peritoneum, fascia, mesenterium, skin, tympanic membrane, other biogenic membranes and vascular wall, oesophageal wall, tracheal wall, urethral wall, ureteral wall, cardiac wall, other external walls of biogenic organs and in addition, fetal membrane, and amnion and chorion which comprise the fetal membrane. Human amnion is approximately 12,000 nanometer in thickness, has a basal layer (50–80 nanometer thick) and a compact layer (8,000–10,000 nanometer thick) as a boundary layer, and contains an epithelial layer and a fibroblast layer on each outer side. The "substantially compact layer" employed in the present specification means the compact layer and the basement membrane layer together in the field of microscopic science and substantially means the compact layer, a term used in the field of physiology.

The quaternary ammonium salt used in the form of an aqueous solution in the invention of the general formula $[C_6H_5CH_2N(CH_3)_2R]^+$ $Cl^-$ is an inverted soap which is capable of sterilization and disinfection (the soap hereafter) and is not a normal detergent. The mechanism of sterilization as described in C-366 (explanation) of the Japan Pharmacopoeia (12th revision), is that an inverted soap, since it is positively charged, is absorbed by negatively charged bacteria and accumulates on the surface of a bacterial body. The bacterial cell protein then becomes denatured. In addition, a solution of an inverted soap diluted at adequate concentrations is a safe and effective sterilizing and disinfecting agent which is used extensively without damaging biogenic tissues including washing of the vagina and bladder and sterilization and disinfection of surgical wounds.

In the Biochemical Dictionary published by Tokyo Kagakudojin Co., Ltd., thiolprotease (the protease hereafter) used in the practice of the invention is described as a glycoprotein having a molecular weight of approximately 26,000 and an isoelectric point of 9 which demonstrates an ideal enzyme activity at around neutral pH value.

The invention can be practiced as follows. In biogenic connective tissue, layers of a cellular nature including epithelial and fibroblast layers exist on both sides of a membranous layer that substantially comprises the compact layer. These cells, like bacterial cells, are made of proteins and contain many negatively charged side chain groups. By soaking biogenic connective tissue membrane in an aqueous solution of the positively charged inverted soap, the biogenic connective tissue membrane is charged positively and denatured gradually starting at the cellular layer on both sides of the membrane in the same manner as the above-described mechanism of sterilization by the inverted soap. The concentration of the inverted soap is not critical and 0.01 to 1% is generally practical. The temperature is not very critical, either, but room temperature or a temperature slightly below or above (e.g., 10–30° C.) may also be employed.

Protein layers of thus denatured biogenic connective tissue membrane are degraded in treatment at pH about 7 with the protease, the proteolysis activity of which is most active in a potential environment near neutral pH. It is natural that the proteolysis will proceed to degrade the compact layer which is made up of collagen, and scleroprotein, unless adequate steps are taken to control proteolysis. Conservation and retention of the compact layer should be attempted by controlling conditions including temperature and time. Room temperature is most practical, but a temperature slightly below or above (e.g., 10–30° C.) may also be employed. The amount of the protease is not very critical as far as the matrix structure of the compact layer is maintained and the epithelial and fibroblast layers are substantially removed. Ficin is a preferred thiolprotease and may be used together with $NaN_3$, preferably a buffer. Ultrasonic washing is the next procedure. By ultrasonic washing, degradation products of epithelial and fibroblast layers adhering to the compact layer are removed, and the membranous material which is composed substantially of the compact layer is acquired.

The invention is described below in further detail by examples. It should be noted that the scope of the invention is not limited to these examples.

Example 1

In a delivery room, using a scissors, only fetal membrane was resected and detached from the placenta using a scissors, the fetal membrane and umbilical cord being passed from a noninfectious mother who had just given birth. The detached fetal membrane was washed under running pharmacopoeial physiological saline as the primary operation of removal and elimination of blood. When, after the primary removal and elimination of blood, the fetal membrane was soaked and placed natant in a solution of the above-described invert soap at room temperature, the amnion had almost peeled off, and chorion was easily detached as tissues between chorion and Desidua capsularis became swollen. By carefully detaching manually, amnion and chorion in such a state were separated and divided completely. As examples for demonstration, amnion is employed in the following procedures.

After being soaked again in pharmacopoeial physiological saline at room temperature and thoroughly washed and rubbed, amnion was washed under running pharmacopoeial physiological saline as the secondary operation of removal and elimination of blood. Following these operations, amnion was suspended in a water tank of an ultrasonic washer filled with overflowing pharmacopoeial purified-water and received ultrasonic washing at room temperature at a frequency of 40 $KH_2$ for 15 minutes. The cleaned amnion thus acquired was tested by Lowry's method. No free protein was found.

Amnion from which blood was removed and eliminated completely was soaked at room temperature for 30 minutes or longer in 0.1% benzalkonium chloride solution, a pharmacopoeial sterilizing disinfectant. After that the amnion was soaked for 24 hours in 0.01% ficin in 0.2 M phosphate buffer solution (pH 7.4) containing 0.05% (W/V) $NaN_3$'. After the ficin treatment, the membranous material was suspended in a water tank of an ultrasonic washer filled with pharmacopoeial purified-water to overflow and then was treated with ultrasonic washing at room temperature at a frequency of 40 KHz for 15 minutes.

The acquired membranous material was acellular in nature and a hydrous membranous material which is composed substantially of a characteristic compact layer retained in tact. The hydrous membranous material was dried in an aseptic vacuum dryer at 35° C. for 12 hours to produce the membranous material of the invention.

Figure 2:
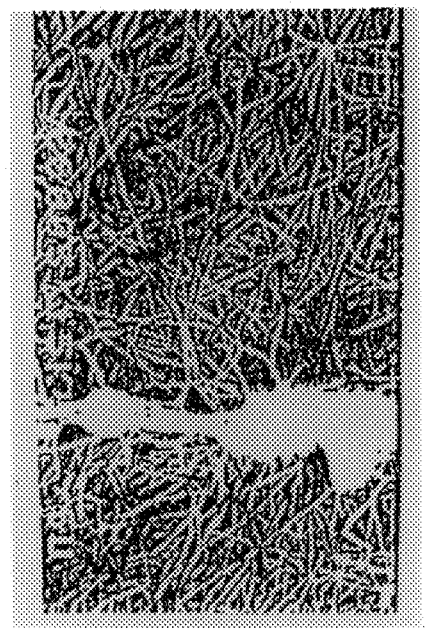
FIG. 2 is an enlarged photograph (5,500×) of a part framed in FIG. 1.
Figure 3:
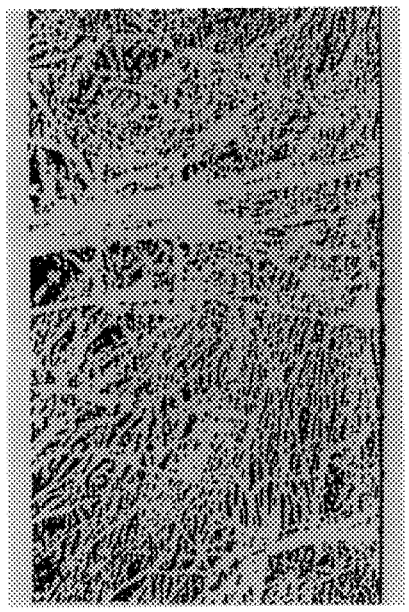
FIG. 3 is an electron microscopy photograph (1,100×) of the back surface of the product produced in Example 1.
Figure 4:
FIG. 4 is an enlarged photograph (5,500×) of a part framed in FIG. 3.

Examination of the front and back surfaces of the membranous material under an electron microscope revealed that the front and back were asymmetrical as shown in FIGS. 1, 2, 3 and 4.

The acquired compact layer membrane of human amnion was imbedded in the muscles of the backs of rabbits to measure absorbency and tissue reaction. Results are shown in Tables 1 and 2.

TABLE 1

Absorption of the compact layer membrane originated from human amnion in muscle at back region of rabbits

| Duration | 2 Weeks | 4 Weeks | 6 Weeks |
| --- | --- | --- | --- |
| Compact layer membrane | Membrane embrittlement 3/5 Breakage of membrane 2/5 | Membrane absorption 3/4 Partial persistence of membrane 1/4 | Membrane absorption 3/3 |

| Duration | 8 Weeks | 12 Weeks | 16 Weeks |
| --- | --- | --- | --- |
| Compact layer membrane | Membrane absorption 3/3 | Membrane absorption 3/3 | Membrane absorption 3/3 |

TABLE 2

Tissue reaction of the compact layer membrane originated from human amnion in muscle of back region of rabbits

| Duration | 2 Weeks | 4 Weeks | 6 Weeks |
| --- | --- | --- | --- |
| Compact layer membrane | Infiltration of inflammatory cells mild 4/5 moderate 1/5 | Infiltration of inflammatory cells very mild 2/4 (including eosinophil) Fibrous change 2/4 | Infiltration of inflammatory cells very mild 2/3 (including eosinophil) Fibrous change 1/3 |

| Duration | 8 Weeks | 12 Weeks | 16 Weeks |
| --- | --- | --- | --- |
| Compact layer membrane | Adipose tissue partial fibrous tissue 3/3 | Adipose tissue partial fibrous tissue 3/3 | Adipose tissue partial fibrous tissue 3/3 |

Tables 1 and 2 show the results of experiments using animals according to clinical tests criteria and manufacture approval criteria relating to the product of the present invention. The product according to the present invention was implanted in muscles at back region of male white rabbits. Tissue samples of the implanted region were taken every two weeks after the implantation and the samples were observed and evaluated according to standard methods of experimental pathology.

The results in Table 1 indicate that the implanted test product was being decomposed and absorbed in the living body for 6 weeks after the implantation, and demonstrate that the decomposition and absorption of the implanted test product was complete in 6 weeks from the implantation. In other words, these results show the progress in which the implanted test product becomes homogenized with the living body while the test product is decomposed and absorbed in the living body and in which the muscle tissues around the implanted product in the rabbit back region regenerate themselves and replace the implanted product, as well as the completed conditions of the progress. The results demonstrate the usefulness of the test product as a medical material.

The results in Table 2 indicate that no generation of abnormal cells such as deformed or cancerous cells was observed with respect to the tissue samples periodically taken and prepared as shown in Table 2. These results demonstrate the safety of the test product.

What is claimed as new and desired to be secured by Letters Patent of the United States is:

1. A method for manufacturing a raw membrane material, comprising the steps of:

(i) positively charging and denaturing biogenic connective tissue which comprises epithelium, basement membrane, compact and fibroblast layers with an aqueous solution of a quaternary ammonium salt of the formula:

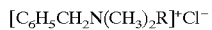

wherein R is an alkyl group of 8 to 10 carbon atoms;

(ii) treating the biogenic connective tissue at a pH of about 7 with thiolprotease which is a glycoprotein having a molecular weight of approximately 26,000 and an isoelectric point of 9; and (iii) thereafter, subjecting the biogenic connective tissue obtained from step (ii) to ultrasonic washing with water, thereby producing said raw membrane material having an acellular nature and consisting essentially of the compact layer of said biogenic connective tissue starting material employed in step (i).

2. The method of claim 1, wherein the biogenic connective tissue is human amnion.

3. The method of claim 2, wherein the front and back faces of the connective tissue are asymmetric to each other.

4. The method of claim 1, wherein the thiolprotease is ficin.

5. The method of claim 4, wherein said ficin is combined with $NaN_3$ in a phosphate buffer.

6. A raw membrane material having an acellular nature and consisting essentially of a compact layer, having front and back faces, whose characteristic matrix structure is retained intact and having front and back faces, said compact layer being produced by dissolving and removing the cellular layers of the epithelial layer, the basement membrane, the fibroblast layer and the spongy layer, leaving the compact layer intact, from a biogenic connective tissue.

7. The raw membrane material of claim 6, wherein said biogenic connective tissue is mater encephali, pericardium pleura, pelvic peritoneum, diaphragm, peritoneum, fascia, mesenterium, skin, tympanic membrane, or vascular, oesophageal, tracheal, urethral, ureteral or cardia wall material, fetal membrane, amnion or chorion.

8. The raw membrane material of claim 6, wherein the biogenic connective tissue is human amnion.

9. The raw membrane material of claim 8, wherein the membrane material is asymmetric with respect to said front and back faces.

* * * * *